United States Patent [19]

Rajadhyaksha

[11] Patent Number: 5,030,629

[45] Date of Patent: Jul. 9, 1991

[54] COMPOSITIONS AND METHOD COMPRISING HETEROCYCLIC COMPOUNDS CONTAINING TWO HETEROATOMS AS MEMBRANE PENETRATION ENHANCERS

[76] Inventor: Vithal J. Rajadhyaksha, 27436 Esquina, Mission Viejo, Calif. 92691

[21] Appl. No.: 393,584

[22] Filed: Aug. 11, 1989

Related U.S. Application Data

[63] Continuation-in-part of Ser. No. 2,387, Jan. 12, 1987, Pat. No. 4,876,249, and a continuation-in-part of Ser. No. 345,457, May 1, 1989, abandoned.

[51] Int. Cl.$^5$ ............... A61K 31/415; A61K 31/42; A61K 31/495; A61K 31/535
[52] U.S. Cl. ...................... 514/211; 514/228.8; 514/256; 514/275; 514/356; 514/374; 514/376; 514/377; 514/385; 514/392; 514/423; 514/470; 514/652; 514/772; 514/788; 514/946; 514/947
[58] Field of Search ............... 514/772, 788, 946, 947, 514/228.8, 256, 274, 275, 211, 356, 392, 423, 470, 652, 385, 374, 376, 377

[56] References Cited

U.S. PATENT DOCUMENTS 4,876,249 10/1989 Rajadhyaksha ............... 514/174
4,960,771 10/1990 Rajadhyaksha ............... 514/228.8

*Primary Examiner*—Shah: Mukund J.
*Assistant Examiner*—Philip I. Datlow

[57] ABSTRACT

A method and compositions for enhancing absorption of topically administered physiologically active agents through the skin and mucous membranes of humans and animals in a transdermal device or formulation for local or systemic use, comprising a therapeutically effective amount of a pharmaceutically active agent and a non-toxic, effective amount of penetration enhancing agent of the formula I:

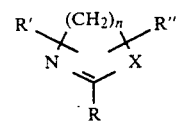

wherein R is a saturated or unsaturated, straight or branched, cyclic or acyclic hydrocarbon group with from 1 to 19 carbon atoms, alkoxyalkyl, haloalkyl, specifically trifluoromethyl, alkoxy, amino, alkylamino and acylamino; R' and R'' are hydrogen, alkyl, trifluoromethyl, alkoxyalkyl, aminoalkyl, alkyl- and acylaminoalkyl, carboxy, carbalkoxy, hydroxyalkyl or lower alkyl ester thereof; X is O or $NR_1$ wherein $R_1$ is hydrogen, alkyl, alkenyl, alkoxyalkyl, carbalkoxyalkyl, aminoalkyl, alkyl- and acylaminoalkyl, hydroxyalkyl or hydroxyalkyloxyalkyl and lower alkyl ester thereof; and n is 2 or 3 are disclosed.

7 Claims, No Drawings

COMPOSITIONS AND METHOD COMPRISING HETEROCYCLIC COMPOUNDS CONTAINING TWO HETEROATOMS AS MEMBRANE PENETRATION ENHANCERS

CROSS-REFERENCE TO RELATED APPLICATIONS

This is a continuation-in-part of my copending application Ser. No. 07/002,387, filed Jan. 12, 1987, which is now U.S. Pat. No. 4,876,249 and my copending application Ser. No. 07/345,457, filed May 1, 1989, now abandoned, and to which priority is claimed.

FIELD OF THE INVENTION

This invention relates to substituted oxazolines and imidazolines as permeation enhancers for pharmaceutical, agricultural and cosmetic agents.

BACKGROUND OF THE INVENTION

Many physiologically active agents are best applied topically to obtain desirable results. Topical application, in the form of creams, lotions, gels, solutions, etc., largely avoids side effects of the agents and permits high level concentrations of the agents.

Some therapeutic drugs may also be administered for systemic use through the skin or other body membranes including intransal and intravaginal application of humans and other animals, utilizing a transdermal device or formulated in a suppository or aerosol spray. For some years, pharmaceutical researchers have sought an effective means of introducing drugs into the bloodstream by applying them to the unbroken skin. Among other advantages, such administration can provide a comfortable, convenient and safe way of giving many drugs now taken orally or infused into veins or injected intramuscularly.

Using skin as the portal for drug entry offers unique potential, because transdermal delivery permits close control over drug absorption. For example, it avoids factors that can cause unpredictable absorption from gastrointestinal tract, including changes in acidity, motility, and food content. It also avoids initial metabolism of the drug by the liver known as the first pass effect. Thus, controlled drug entry through skin can achieve a high degree of of control over blood concentrations of drug. Close control over drug concentration in blood can translate readily into safer and more comfortable treatment. When a drug's adverse effects occur at higher concentrations than its beneficial ones, rate control can maintain the concentration that evoke only-or principally the drug's desired actions. This ability to lessen undesired drug actions can greatly reduce the toxicity hazards that now restrict or prevent the use of many valuable agents.

Transdermal delivery particularly benefits patients with chronic disease. Many such patients have difficulty following regimens requiring several doses daily of medications that repeatedly cause unpleasant symptoms. They find the same drugs much more acceptable when administered in transdermal system that require application infrequently-in some cases, only once or twice weekly-and reduce adverse effects.

Transdermal delivery is feasible for drugs effective in amounts that can pass through the skin area and that are substantially free of localized irritating or allergic effects. While these limitations may exclude some agents, many others remain eligible for transdermal delivery. Moreover, their numbers will expand as pharmaceutical agents of greater potency are developed. Particularly suitable for transdermal delivery are potent drugs with only a narrow spread between their toxic and safe blood concentrations, those having gastrointestinal absorption problems, those susceptible to a higher first pass liver metabolism or those requiring frequent dosing in oral or injectable form.

Transdermal therapy permits much wider use of natural substances such as hormones. Often the survival times of these substances in the body are so short that they would have to be taken many times daily in ordinary dosage forms. Continuous transdermal delivery provides a practical way of giving them, and one that can mimic the body's own patterns of secretion.

At present, controlled transdermal therapy appears feasible for many drugs used for a wide variety of ailments including, but not limited to, circulatory problems, hormone deficiency, respiratory ailments, and pain relief.

Percutaneous administration can have the advantage of permitting continuous administration of drug to the circulation over prolonged periods of time to obtain a uniform delivery rate and blood level of drug. Commencement and termination of drug therapy are initiated by the application and removal of the dosing devices from the skin. Uncertainties of administration through the gastrointestinal tract and the inconvenience of administration by injection are eliminated. Since a high concentration of drug never enters the body, problems of pulse entry are overcome and metabolic half-life is not a factor of controlling importance.

The greatest problems in applying physiologically active agents topically or transdermally is that the skin is an effective barrier to penetration. The epidermis of the skin has an exterior layer of dead cells called the stratum corneum which is tightly compacted and oily and which provides an effective barrier against gaseous, solid or liquid chemical agents, whether used alone or in water or in oil solutions. If a physiologically active agent penetrates the stratum corneum, it can readily pass through the basal layer of the epidermis and into the dermis.

Although the effectiveness of the stratum corneum as a barrier provides great protection, it also frustrates efforts to apply beneficial agents directly to local areas of the body. The inability of physiologically active agents to penetrate the stratum corneum prevents their effective use of treating such conditions as inflammation, acne, psoriasis, herpes labialis, herpes genitalis, eczema, infections caused by fungi, viruses and other microorganisms, or other disorders or conditions of the skin or mucous membranes or of conditions beneath the exterior surface of the skin or mucous membranes. The stratum corneum also prevents the skin from absorbing and retaining cosmetic-type materials such as sunscreens, perfumes, mosquito repellents and the like.

Physiologically active agents may be applied to the locally affected parts of the body in the form of a solution, cream, lotion or gel utilizing the vehicle system described herein. These agents may also be delivered for systemic use utilizing the vehicle system in a transdermal patch. Vehicles such as USP cold cream, ethanol and various ointments, oils, solvents and emulsions have been used heretofore to apply physiologically active ingredients locally. Most such vehicles are not effective to carry significant amounts of physiologically active agents into and through the skin. One such vehicle is dimethyl sulfoxide, which is described in U.S. Pat. No. 3,551,554.

My previous inventions disclosed in U.S. Pat. Nos. 3,989,816; 3,991,203; 4,122,170; 4,316,893; 4,415,563; 4,423,040; 4,424,210; 4,444,762 describe a method for enhancing the topical administration of physiologically active agents by combining such an agent with an effective amount of a penetration enhancer and applying the combination topically to humans or animals, in the form of solution, cream, gel, lotion etc. This prior art discloses N-alkyl substituted cyclic lactams as penetration enhancers.

My related U.S. Pat. No. 4,405,616 describes a method for administering systemically active agents through the skin or other body membranes of humans and animals, utilizing a transdermal device or formulation containing an effective amount of a suitable membrane penetration enhancer selected from the disclosed N-alkyl substituted cyclic lactams.

My related U.S. Pat. Nos. 4,461,638 and 4,762,549 describe a method for enhancing delivery of plant nutrients and plant growth regulators, and my U.S. Pat. No. 4,525,199 describes an improved method of pest control by enhancing pesticide permeation.

My related U.S. application, Ser. No. 783,621, now U.S. Pat. No. 4,837,026, filed on Sept. 30, 1985, describes a method for enhancing topical and transdermal administration of physiologically active agents with membrane penetration enhancers selected from the alkanoic acid cyclic amides disclosed therein.

My related U.S. application, Ser. No. 002,387, filed on Jan. 12, 1987, describes a method for enhancing topical and transdermal administration of physiologically active agents with membrane penetration enhancers selected from heterocyclic compounds containing two heteroatoms.

My related U.S. application, Ser. No. 218,316, filed on Jul. 12, 1988, describes a method for enhancing topical and transdermal administration of physiologically active agents with membrane penetration enhancers selected from oxazolidone and related heterocyclic compounds.

My related U.S. application Ser. No. 07/345,457, filed on May 1, 1989, describes a method for enhancing topical and transdermal administration of physiologically active agents with membrane penetration enhancers selected from substituted imidazolines.

My related U.S. application Ser. No. 07/348,387, filed on May 8, 1989 describes a method for enhancing topical and transdermal administration of physiologically active agents with yet another series of membrane penetration enhancers.

Penetration enhancers for enhancing systemic administration of therapeutic agents transdermally disclosed in the art include dodecyl pyrrolidone, dimethyl lauramide and dimethyl sulfoxide. These agents may be used prior to or concurrently with administration of the active agent, see, e.g., U.S. Pat. Nos. 4,031,894; 3,996,934 and 3,921,636.

SUMMARY OF THE INVENTION

The invention relates to compositions for carrying physiologically active agents through body membranes such as skin and for retaining these agents in the body tissues and further relates to a method of administering systemically active agents through the skin or other body membranes of humans and animals, utilizing a transdermal device or formulation, containing an effective, non-toxic amount of a membrane penetration enhancer having the structural formula I:

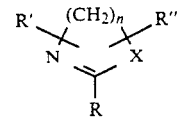

wherein:

R is a saturated or unsaturated, straight or branched, cyclic or acyclic hydrocarbon group with from 1 to 19 carbon atoms, alkoxyalkyl, haloalkyl, specifically trifluoromethyl, alkoxy, amino, alkylamino and acylamino.

R' and R" are hydrogen, alkyl, trifluoromethyl, alkoxyalkyl, aminoalkyl, alkyl- and acylaminoalkyl, carboxy, carbalkoxy, hydroxyalkyl or lower alkyl ester thereof.

X is O or $NR_1$, wherein $R_1$ is Hydrogen, alkyl, alkenyl, alkoxyalkyl, aminoalkyl, alkyl- and acylaminoalkyl, hydroxyalkyl and hydroxyalkyloxyalkyl or lower alkyl ester thereof; and n is 2 or 3.

In one preferred embodiment of I, R' and R" are H; X is O; R and n being as defined. The preferred compounds of this embodiment are:
2-(2-dodecyl)-2-oxazoline,
2(2-methyl-2-decyl)-2-oxazoline,
2[1-(3-oxaundecyl)]-2-oxazoline In another preferred embodiment of the composition I, R' is Hydrogen, R" is alkyl, alkoxyalkyl, trifluoromethyl, carboxy, carbalkoxy, hydroxyalkyl or alkyl esters thereof, X is O and R and n being as defined. The preferred compounds of this embodiment are:
4-Methyl-2-(2-dodecyl)-2-oxazoline,
4-Isopropyl-2-(2-dodecyl)-2-oxazoline,
4-Trifluoromethyl-2-(2-dodecyl)-2-oxazoline,
4-Isopropyl-2-(2-methyl-2-decyl)-2-oxazoline,
4-Decyl-2-trifluoromethyl-2-oxazoline,
4-[1-(2-Oxadodecyl)]-2-methyl -2-oxazoline,
4-[1-(2-Oxadodecyl)]-2-trifluoromethyl-2-oxazoline,
5-[1-(2-Oxadodecyl)]-2-trifluoromethyl-2-oxazoline,
4-Hydroxymethyl-2-undecyl-2-oxazoline,
4-Trimethylacetoxymethyl-2-undecyl-2-oxazoline,
4-Carbethoxy-2-undecyl-2-oxazoline,
4-Dodecyl-2-ethoxy-2-oxazoline.

In yet another preferred embodiment of I, R' and R" are selected from alkyl, alkoxyalkyl, trifluoromethyl, carboxy, carbalkoxy, hydroxyalkyl and alkyl esters thereof; X is O; R and n being as defined. The preferred compounds of this embodiment are:
4,4-Dimethyl-2-undecyl-2-oxazoline,
4-Methyl-4-trifluoromethyl-2-undecyl-2-oxazoline,
4,4-Dimethyl-2-(1-dodecen-2-yl)-2-oxazoline,
4-Methyl-4-trifluoromethyl-2-(1-dodecen-2-yl)2-oxazoline,
4,4-Dimethyl-2-(2-dodecyl)-2-oxazoline,
4,4-Dimethyl-2-(2-methyl-2-decyl)-2-oxazoline,
4,4-Dimethyl-2-[1-(3-oxaundecyl)]-2-oxazoline,
4-Hydroxymethyl-4-methyl-2-undecyl-2-oxazoline,
4-Hydroxymethyl-4-trifluoromethyl-2-undecyl-2-oxazoline,
4-Trimethylacetoxymethyl-4-methyl-2-undecyl-2-oxazoline,
4-Hydroxymethyl-4-methyl-2-(2-dodecyl)-2-oxazoline,
4-Hydroxymethyl-4-methyl-2-(2-methyl-2-decyl)-2-oxazoline, 4-Trimethylacetoxymethyl-4-methyl-2-(2-dodecyl)-2-oxazoline,
4-Trimethylacetoxymethyl-4-methyl-2-(2-methyl-2-decyl)-2-oxazoline,
4-Carboxy-4-methyl-2-undecyl-2-oxazoline,
4-Carbethoxy-4-methyl-2-undecyl-2-oxazoline,
4-Methyl-4-[1-(2-oxadodecyl)]-2-trifluoromethyl-2-oxazoline, and
4-Methyl-4-dodecanoyloxymethyl-2-trifluoromethyl-2-oxazoline.

In another preferred embodiment of I, R' and R" are H; X is $NR_1$, n, R and $R_1$ being as defined. The preferred compounds of this embodiment are:
2-Undecyl-2-imidazoline,
1-Methyl-2-heptyl-2-imidazoline,
1-Isopropyl-2-undecyl-2-imidazoline,
1-(2-Hydroxyethyl)-2-undecyl-2-imidazoline,
1-(2-Hydroxyethyl)-2-(heptadec-8-enyl)-2-imidazoline,
1-[2-(Trimethylacetoxy)ethyl]-2-undecyl-2-imidazoline, and
1-(2-ethoxyethyl)-2-undecyl-2-imidazoline,
1-[2-(2-Hydroxyethoxy)ethyl]-2-undecyl-2-imidazoline,
1-(2-Carbethoxyethyl)-2-undecyl-2-imidazoline and
1-Dodecyl-2-trifluoromethyl-2-imidazoline.

In another preferred embodiment of the composition I, R' is Hydrogen, R" is alkyl or trifluoromethyl; X is $NR_1$; n, R and $R_1$ being as defined. The preferred compounds of this embodiment are:
4-Methyl-2-undecyl-2-imidazoline,
4-Isopropyl-2-undecyl-2-imidazoline,
4-t-Butyl-2-undecyl-2-imidazoline,
4-Trifluoromethyl-2-undecyl-2-imidazoline,
1,4-Diisopropyl-2-undecyl-2-imidazoline,
4-Methyl-1-isopropyl-2-undecyl-2-imidazoline,
4-Methyl-2-(2-dodecyl)-2-imidazoline,
4-Methyl-2-(2-methyl-2-decyl)-2-imidazoline,
4-Decyl-2-trifluoromethyl-2-imidazoline and
4-Decyl-2-ethoxy-2-imidazoline.

In yet another preferred embodiment of I, R' and R" are alkyl or trifluoromethyl; X is $NR_1$; n, R and $R_1$ being as defined. The preferred compounds of this embodiment are:
4,4-Dimethyl-2-undecyl-2-imidazoline,
4-Methyl-4-t-butyl-2-undecyl-2-imidazoline,
4,4-Dimethyl-1-isopropyl-2-undecyl-2-imidazoline,
4-Methyl-1,4-diisopropyl-2-undecyl-2-imidazoline,
4,4-Dimethyl-2-(2-dodecyl)-2-imidazoline,
4,4-Dimethyl-1-isopropyl-2-(2-dodecyl)-2-imidazoline,
4,4-Dimethyl-2-(2-methyl-2-decyl)-2-imidazoline,
4,4-Dimethyl-1-isopropyl-2-(2-methyl-2-decyl)-2-imidazoline.

It has been found that the physiologically active agents are carried through body membranes by the claimed penetration enhancers and are retained in the body tissue when applied topically in form of a cream, gel, or lotion or absorbed systemically when applied in the form of a transdermal device or formulation, for example, as a transdermal patch, a rectal or vagina suppository, as a nasal spray or when incorporated in a vaginal sponge or tampon.

DETAILED DESCRIPTION OF THE INVENTION

Typical examples of compounds included in the foregoing formula I of this invention are the following:
1. 4-Trifluoromethyl-2-undecyl-2-oxazoline;
2. 4-Isopropyl-2-nonyl-2-oxazoline;
3. 4-Isopropyl-2-undecyl-2-oxazoline;
4. 4-t-Butyl-2-undecyl-2-oxazoline;
5. 4-Methyl-4-trifluoromethyl-2-undecyl-2-oxazoline;
6. 4-Methyl-4-isopropyl-2-undecyl-2-oxazoline;
7. 4-Methyl-4-t-butyl-2-undecyl-2-oxazoline;
8. 4-Trifluoromethyl-2-(1-dodecen-2-yl)-2-oxazoline;
9. 4,4-Dimethyl-2-(1-dodecen-2-yl)-2-oxazoline;
10. 4-methyl-4-trifluoromethyl-2-(1-dodecen-2-yl)-2-oxazoline;
11. 4-Hydroxymethyl-4-trifluoromethyl-2-undecyl-2-oxazoline;
12. 4-Trimethylacetoxymethyl-4-methyl-2undecyl-2-oxazoline;
13. 2-(2-decyl)-2-oxazoline;
14. 2-(2-dodecyl)-2-oxazoline;
15. 4-Methyl-2-(2-dodecyl)-2-oxazoline;
16. 4-Isopropyl-2-(2-dodecyl)-2-oxazoline;
17. 4-t-Butyl-2-(2-dodecyl)-2-oxazoline;
18. 4-Trifluoromethyl-2-(2-dodecyl)-2-oxazoline;
19. 4,4-Dimethyl-2-(2-dodecyl)-2-oxazoline;
20. 4-Methyl-4-isopropyl-2-(2-dodecyl)-2-oxazoline;
21. 4-Methyl-4-t-butyl-2-(2-dodecyl)-2-oxazoline;
22. 4-Methyl-4-trifluoromethyl-2-(2-dodecyl)-2-oxazoline;
23. 4-Hydroxymethyl-4-methyl-2-(2-dodecyl)-2-oxazoline;
24. 4-[2-(Trimethylacetoxy)ethyl]-4-methyl-2-(2-dodecyl)-2-oxazoline;
25. 2-(2-methyl-2-decyl)-2-oxazoline;
26. 2-(2-methyl-2-dodecyl)-2-oxazoline;
27. 4-Trifluoromethyl-2-(2-methyl-2-decyl)-2-oxazoline;
28. 4,4-Dimethyl-2-(2-methyl-2-decyl)-2-oxazoline;
29. 4,4-Dimethyl-2-(2-methyl-3-tridecyl)-2-oxazoline;
30. 2-[1-(3-Oxaundecyl)]-2-oxazoline;
31. 4-Decyl-2-trifluoromethyl-2-oxazoline;
32. 4-[1-(2-Oxadodecyl)]-2-methyl-2-oxazoline;
33. 4-[1-(2-Oxadodecyl)]-2-trifluoromethyl-2-oxazoline;
34. 5-[1-(2-Oxadodecyl)]-2-trifluoromethyl-2-oxazoline;
35. 4-Hydroxymethyl-2-undecyl-2-oxazoline;
36. 4-Trimethylacetoxymethyl-2-undecyl-2-oxazoline;
37. 4-Carbethoxy-2-undecyl-2-oxazoline;
38. 4,4-Dimethyl-2-[1-(3-oxaundecyl)]-2-oxazoline;
39. 4-Carboxy-4-methyl-2-undecyl-2-oxazoline;
40. 4-Carbethoxy-4-methyl-2-undecyl-2-oxazoline;
41. 4-Methyl-4-[1-(2-oxadodecyl)]-2-trifluoromethyl-2-oxazoline;
42. 4-Methyl-4-dodecanoyloxymethyl-2-trifluoromethyl-2-oxazoline;
43. 4-Methyl-2-nonyl-2-oxazoline;
44. 4-Methyl-2-undecyl-2-oxazoline;
45. 4,4-Dimethyl-2-nonyl-2-oxazoline;
46. 4,4-Dimethyl-2-undecyl-2-oxazoline;
47. 4,4-Dimethyl-2-tridecyl-2-oxazoline;
48. 4-Hydroxymethyl-4-methyl-2-nonyl-2-oxazoline;
49. 4-Hydroxymethyl-4-methyl-2-undecyl-2-oxazoline;
50. 4-Hydroxymethyl-4-ethyl-2-undecyl-2-oxazoline;
51. 2-Pentyl-2-oxazoline;
52. 2-Heptyl-2-oxazoline;
53. 2-Nonyl-2-oxazoline;
54. 2-Undecyl-2-oxazoline;
54. 2-Tridecyl-2-oxazoline;
55. 2-Pentadecyl-2-oxazoline;
56. 2-Heptadecyl-2-oxazoline;
57. 2-Undecyl-2-imidazoline;
58. 1-Isopropyl-2-pentyl-2-imidazoline;
59. 1-Methyl-2-heptyl-2-imidazoline;
60. 1-Methyl-2-undecyl-2-imidazoline;
61. 1-(2-Hydroxyethyl)-2-undeyl-2-imidazoline;

62. 1-[2-(Trimethylacetoxy)ethyl]-2-undeyl-2-imidazoline;
63. 1-Isopropyl-2-undecyl-2-imidazoline;
64. 4-Methyl-2-undecyl-2-imidazoline;
65. 4-Isopropyl-2-undecyl-2-imidazoline;
66. 4-Trifluoromethyl-2-undecyl-imidazoline;
67. 1,4-Diisopropyl-2-undecyl-2-imidazoline;
68. 4-t-Butyl-1-isopropyl-2-undecyl-2-imidazoline;
69. 4,4-Dimethyl-2-undecyl-2-imidazoline;
70. 4-Methyl-4-isopropyl-2-undecyl-2-imidazoline;
71. 4-Methyl-4-t-butyl-2-undecyl-2-imidazoline;
72. 4,4-Diisopropyl-2-undecyl-2-imidazoline;
73. 4-Methyl-4-trifluoromethyl-2-undecyl-2-imidazoline;
74. 4,4-Dimethyl-1-isopropyl-2-pentyl-2-imidazoline;
75. 4,4-Dimethyl-1-isopropyl-2-undecyl-2-imidazoline;
76. 4,4-Dimethyl-1-(2-hydroxyethyl)-2-undecyl-2-imidazoline;
77. 4,4-Dimethyl-1-[2-(Trimethylacetoxy)ethyl]-2-undecyl -2-imidazoline;
78. 4,4-Dimethyl-1-(1-hydroxy-2-methyl-2-propyl)-2-undecyl-2-imidazoline;
79. 4,4-Dimethyl-1-(1acetoxy-2-methyl-2-propyl)-2-undecyl-2-imidazoline;
80. 2-(2-dodecyl)-2-imidazoline;
81. 1-(2-Hydroxyethyl)-2-(2dodecyl)-2-imidazoline;
82. 1-[2-(Trimethylacetoxy)ethyl]-2-(2-dodecyl)-2-imidazoline;
83. 1-Isopropyl-2-(2-dodecyl)-2-imidazoline;
84. 4,4-Dimethyl-2-(2-dodecyl)-2-imidazoline;
85. 4,4-Dimethyl-1-isopropyl-2-(2-dodecyl)-2-imidazoline;
86. 2-(1-Dodecen-2-yl)-2-imidazoline;
87. 1-Isopropyl-2-(1-dodecen-2-yl)-2-imidazoline;
88. 4,4-Dimethyl-2-(1-dodecen-2-yl)-2-imidazoline;
89. 4,4-Dimethyl-1-isopropyl-2-(1-dodecen-2-yl)-2-imidazoline;
90. 2-(2-methyl-2-decyl)-2-imidazoline;
91. 1-(2-Hydroxyethyl)-2-(2-methyl-2-decyl)-2-imidazoline;
92. 4,4-Dimethyl-2-(2-methyl-2-decyl)-2-imidazoline;
93. 1-(2-Ethoxyethyl)-2-undecyl-2-imidazoline;
94. 4,4-Dimethyl-1-(2-ethoxyethyl)-2-undecyl-2-imidazoline;
95. 1-(2-Diethylaminoethyl)-2-undecyl-2-imidazoline;
96. 1-(2-Hydroxyethyl)-2-(heptadec-8-enyl)-2-imidazoline;
97. 1-(2-Carbethoxyethyl)-2-undecyl-2-imidazoline;
98. 1-[2-(2-Hydroxyethoxy)ethyl]-2-undecyl-2-imidazoline;
99. 1-Dodecyl-2-trifluoromethyl-2-imidazoline;
100. 4-Decyl-2-trifluoromethyl-2-imidazoline;
101. 4-Dodecyl-2-ethoxy-2-imidazoline;
102. 4-Dodecyl-2-ethoxy-2-oxazoline;
and esters of the hydroxy substituted compounds listed.

The following 2-oxazolines, encompassed by general formula I of this invention are known in the literature. Compounds 46, 48 and 49 were evaluated for phytotoxicity [Allen and Skoog, Plant Physiol. 26, 611 (1951); C.A. 45: 9790f (1951)]; Compounds 52–57 were evaluated for surface activity [Ishii et. al., Yukagaku 7, 70–74 (1958); C.A. 55:5993d (1961)]; Compounds 52 and 54 were used to prepare nitrogen containing polymers useful as adhesive and thickeners for water base paints [Litt et. al., U.S. Pat. No. 3,483,141, Dec. 9, 1969]; Method of preparation for compounds 51, 52, 54 and 57 is disclosed by Litt et. al., U.S. Pat. No. 3,562,263, Feb. 9, 1971; by Bassiri et. al., Polymer Lett. 5,871–9 (1967) and by Levy and Litt, Polymer Lett. 5,881–6 (1967) and for compound 54 by Seeliger and Thier, Justus Liebigs Ann. Chem 698, 158–66 (1966); C.A. 66: 37856x (1967) and by Seeliger et. al., Angew. Chem., Int. Ed. Engl.5, 875–88 (1966); Lactate, citrate and tartrate salts of compounds 45–47 were evaluated for their emulsifying and foaming properties [Kimura et. al., Yukagaku, 21, 197–200 (1972); C.A. 77: 50538s (1972)] and same salts of compounds 48, 49 and their $C_{13}$, $C_{15}$, and $C_{17}$ homologs were evaluated for surface activity [Kimura et. al., Kogyo Kagaku Zasshi, 63,582–5 (1960); C.A.: 58, 11583b (1963); Method of preparation for compound 56 disclosed by Litt et. al. in U.S. Pat. No. 3,681,333, 01 Aug 1972 and compound 56 in a related U.S. Pat. No. 3,681,329 01 Aug 1972; Method of preparation for compounds 51, 54 and 57 is disclosed by Witte and Seeliger, Angew. Chem., Int. Ed. Engl. 11,287–8 (1972) and Liebigs Ann. Chem. 996–1009 (1974); Compounds 45–47 and their $C_5$, $C_7$, $C_{15}$ and $C_{17}$ analogs are disclosed as emulsifiers in polymerization of styrene and butadiene [Frump, U.S. Pat. No. 3,886,128; 27 May 1975; C.A. 83: 180219y (1975)]; Organic acid salts of compounds 53–55 were evaluated for their emulsifying and foaming properties [Kimura et. al., Yukagaku, 24,869–73 (1975); C.A. 84: 137589c (1976)]; compounds 45–47 and their $C_5$, $C_7$, and $C_{15}$ analogs were disclosed and compound 45 was evaluated for antimicrobial activity [Hunsucker, U.S. Pat. No. 4,049,819, 20 Sept. 1977; C.A. 87: 195540c (1977)]; Compound 46 and its $C_5$ and $C_{17}$ analogs are disclosed as intermediates in the synthesis of monoacyl glycerols [Hersloef and Gronowitz, Chem. Scr. 22, 230–5 (1983); C.A. 100: 156203n (1984)]; Erskine and Lydon disclose oxazolines with alkyl groups of 7–19 carbon atoms in 2-position and additionally substituted with alkyl or hydroxyalky groups with 1–3 carbon atoms in 4 and/or 5 position as surfactants in Iron Blue Pigment Composition suitable for incorporating in transfer or carbon paper inks (U.S. Pat. No. 2,893,886, July 7, 1959); Thompson et. al. disclose 2-alkyl-4,4-dimethyl-2-oxazoline salts of lauryl or oleyl phosphoric acid partial esters as antistatic agents in lubricating compositions for textiles (U.S. Pat. No. 2,976,186, Mar 21, 1961); Johnson discloses 2-alkyl substituted oxazolines (7–17 carbon atoms), additionally substituted with alkyl or hydroxymethyl groups in 4 position as antifoaming and emulsifying agents in fermentation processes (U.S. Pat. No. 2,443,825, June 22, 1948) and finally compounds 45–47, 9 and analogs are mentioned as intermediates in the synthesis of alpha-substituted acrylic acids [Serota et. al., J. Org. Chem 46, 4147–4151 (1981)].

The following 2-imidazoline derivatives, encompassed by general formula I of this invention, are known in the literature. Synthesis of compound 57 and other alkyl analogs is reported by Morill (U.S. Pat. No. 2,508,415, May 23, 1950); Compound 57 and nonyl analog were prepared in low yield by Clintwood and Emmet-Ried, J. Amer. Chem. Soc. 57,2424, (1953); Compound 57 and its $C_{17}$ homolog were synthesized by Waldmann and Chwala, Chem. Ber. 74,1763 (1941); French Patent No. 811,423, Apr. 14, 1937; U.S. Pat. No. 2,155,877, Apr. 25, 1939; Compound 57 was prepared by Piskov et al; Khim. Geterotsikl, Soedin., 1112 (1976); C.A. 86,5372h (1977); Bockmuhl and Knoll reported the synthesis of $C_{15}$ and $C_{17}$ substituted 2-imidazolines intended to be useful for therapeutic or technical purposes, U.S. Pat. No. 1,958,529, May 15, 1934; C.A. 28,4539 (1934); Wellman and McCallan have reported 2-heptadecyl-2-imidazoline useful as foliage fungicide; C.A. 40,4470 (1946); Kyrides et. al., J. Org. Chem. 12,577 (1947) and Shepard and Shonle, J. Amer. Chem. Soc. 69,2269 (1947) have reported synthesis of compounds 57, 59, 60 and 1-ethyl and 1-pentyl-2-undecyl-2-imidazolines in low to moderate yields and their bacteriostatic and local anesthetic activity; Mikeska in U.S. Pat. No. 2,361,488; C.A. 39,2190 (1945) discloses 2-imidazolines substituted in 2-position with saturated or unsaturated alkyl group with 10-23 carbon atoms in paving composition; Russell describes the use of 2-imidazolines and specifically claims 2-heptadecyl-2-imidazoline in herbicidal composition, U.S. Pat. No. 2,514,341, July 4, 1950; Compound 74 was prepared by Harnsberger and Riebsomer, J. Hetero. Chem. 1,188 (1964) and Compounds 74, 75 and related alkyl analogs were reported in very low yield by Riebsomer, J. Amer. Chem. Soc. 70,1629 (1948); Compound 57 and its $C_5$, $C_{10}$, $C_{12}$ and $C_{17}$ analogs as well as compound 64 and its $C_{17}$ analog were prepared by Sawa, Nippon Kagaku Zasshi, 89,780 (1968; C.A. 70 19983q (1969). Wilson discloses 1-hydroxyalkyl-2-imidazolines and specifically, 1-hydroxyethyl-2-heptadecyl-2-imidazoline, as surface active agents, U.S. Pat. No. 2,267,965 (Dec. 30, 1941) and U.S. Pat. No. 2,268,273 (Dec. 30, 1941). Tryon reported the preparation of compounds 58, 63 and two higher homologs in very low yield, U.S. Pat. No. 2,520,102 (Aug. 22, 1950). Compounds 61, 96 and the corresponding 2-stearyl and 2-isosterayl analogs are commercially known cationic surface active agents useful as themselves or in the form of their salts in textile auxiliaries, such as softeners, dye assistants, finishing aids and antistatics, in emulsifiable concentrates such as wool oils, paper softeners, cutting oils, metal lubricants, in oil and wax emulsions for polishes and cosmetic creams, in agricultural products such as antifungal sprays, in corrosion inhibitors, where they are used by themselves or in combination with fatty acids, oils and waxes, in organic coatings for improving bonding properties, preventing water sealers, in certain hydrophilic pigments to render them hydrophobic before subsequent milling with oils and esters, in building materials such as concrete, cement and bricks, to make these water repellent, and asphalt to improve its binding properties to gravel, p. 230 in McCutcheon's Emulsifiers and Detergents, 1987 North American Edition, MuCutcheon Division, McCutcheon Publishing Co., 175 Rock Road, Glen Rock, N.J. 07452.

To my knowledge the other compounds are novel.

The use of the compounds of the present invention as penetration enhancers is, however, novel and not predictable from the prior art.

The heterocyclic compounds covered by the general formula I may be prepared by any of the processes known for the preparation of 2-oxazoline derivatives, for example:

1) Heating a nitrile of formula R—CN with an aminoalcohol of the following formula II in presence of cadmium acetate dihydrate or zinc acetate dihydrate at 100°-130° C. with or without a solvent affords the compounds of this invention:

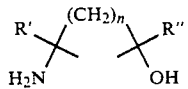  II (wherein R,R' and R are as defined above) [Witte and Seeliger, Angew. Chem., Int. Ed. Eng., 11, 287-8 (1972); Liebigs Ann. Chem 996-1009 (1974)]. Alternately, an allenic or acetylenic nitrile with an aminoalcohol of formula II on heating gives the compounds of this invention [Fomum et. al., Tet. Lett. 1101-4(1975)].

2) A carboxylic acid, R—COOH, is made to react with an aminoalcohol of the formula II with or without solvent at a temperature of from 150° to 250° C. with elimination of water [Serota et. al., J. Org. Chem. 46, 4147-51 (1981); Hersloef and Gronowitz, Chem. Scr. 22,230-5 (1983); Frump, Chem. Rev. 71, 483-505 (1971); Meyers and Mihelich, Angew. Chem., Int. Ed. Eng. 15, 270-281(1976)]. In addition compounds, which possess an exocyclic doublebond on hydrocarbon group R, for example, compounds 8-10, can be prepared according to Serota et. al., J. Org. Chem., 46,4147-51 (1981) from the reaction of 2-alkyl oxazolines with formaldehyde, followed by dehydration. Alternately, aminoalcohol of the formula II may be reacted with an acrylate ester in presence of a catalyst and a polymerization inhibitor, De Benneville and Luskin, U.S. Pat. No. 2,831,858 (Apr. 22, 1958); C.A. 52, 16379h (1958); U.S. Pat. No. 2,897,192 (July 28, 1959); C.A. 54, 585f (1960); Luskin and De Benneville, Ger. Patent No. 1,067,437 (Oct. 22, 1959); C.A. 55, 19960a (1961). In case of unsubstituted aminoalcohols, the resulting amidoalcohols can be cyclodehydrated as under 3.

3) Cyclodehydration of an amidoalcohol of formula III:

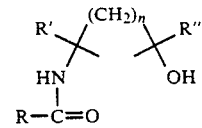 III (wherein R, R' and R" are as defined above) to 2-oxazoline derivative is catalyzed by $WO_3.H_2O$, $NaWO_4.2H_2O$, $MoO_2$ and $SrWO_4$ (Litt et. al., U.S. Pat. No. 3,681,333 and U.S. Pat. No. 3,681,329, 01 Aug 1972) or by silica, alumina, silica-alumina or silica-magnesia at 200°-400° C. under reduced pressure [Litt and Levy, U.S. Pat. No. 3,562,263, Feb 9, 1971; Seeliger and Thier, Justus Liebigs Ann. Chem. 698, 158-66 (1966); Seeliger et. al., Angew. Chem., Int. Ed. Eng. 5, 875-88 (1966)] or by treatment with $SOCl_2$, $RSO_2Cl$, $COCl_2$ or $PO(OR)_2Cl$ in order to replace the hydroxy group by an efficient leaving group that can be eliminated more readily during cyclization [Ishii et. al., Yukagaku, 7, 70-4 (1958); C.A. 55,5993 (1961) and Zioudrou and Schmir, J. Amer. Chem. Soc. 85,3258 (1963)] or simply on heating at high temperature with or without a catalytic amount of a strong mineral acid, De Benneville et al, J. Org. Chem., 23, 1355 (1958).

The amidoalcohol of formula III mentioned above may be prepared from carboxylic acid of formula, R—COOH; from carboxylic acid chloride of formula, R—COCl or from carboxylic acid ester of the formula, R—COOR''' (where R''' is an alkyl group) with an aminoalcohol of formula II mentioned above with or without solvent at a temperature from 0° C. to 150° C. [Wenker, J. Amer. Chem. Soc. 57,1079 (1935); D'Alelio and Emmet-Reid, J. Amer. Chem. Soc. 59,111 (1937); Bassiri et. al., Polymer Lett 5, 871-9 (1967)].

4) Cyclization of the haloamide of the formula IV:

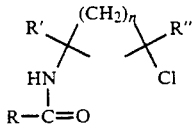

(wherein R, R' and R" are as defined above) with a base such as sodium or potassium hydroxide in aqueous or aqueous alcohol solution or better yet with anhydrous sodium carbonate at an elevated temperature (50° C.–250° C.) under reduced pressure (0.1 mm –30 mm), [Frump, Chem. Rev. 71,483 (1971) and references cited therein; Bassiri, French Pat. 1,477,049, 14 Apr. 1967; Bassiri et.al., Polymer Lett. 5, 871–9 (1967);

5) Addition of an epoxide to a nitrile of the formula, R—CN, in concentrated sulfuric acid gives oxazolines of this invention [Oda et. al., Bull. Soc. Chem. Japan, 35, 1219 (1962)].

6) Reaction of an iminoester with an aminoalcohol of formula II mentioned above affords the penetration enhancers of this invention [McCasland and Horswill, J. Amer. Chem. Soc., 73, 3744 (1951); Dornow and Theidel, Chem. Ber. 88, 1267 (1955); and British Patent 704,946 (1954); C.A. 49, 10370 (1956)].

7) Reaction of an epoxide with an amidine yields oxazolines of this invention [Lambert and Kristofferson, J. Org. Chem., 30,3938 (1965)].

8) Treatment of a carboxylic acid of the formula, R—COOH or a carboxylic acid chloride of the formula, R—COCl with ethyleneimine, followed by catalytic isomerization of the carboxylic acid amide gives the oxazolines of this invention [Kagiya et. al., Polymer Lett., 4, 441–5 (1966); Heine et. al., J. Amer. Chem. Soc., 81 2202 (1959); Fanta and Deutsch, J. Org. Chem., 23,72 (1958); Meyers et. al., J. Org. Chem., 39,2787 (1974); Fukui et. al., Japan 69 22,285 (Sept. 24, 1969); C.A. 71, 12449p (1969)]. 2-Amino substituted derivatives may be prepared according to the method of Meschino and Bond, J. Org. Chem. 28, 3129 (1963) or Najer et. al., Bull. Soc. Chim. Fr. 1609 (1959) and references cited therein.

The heterocyclic compounds covered by the general formula I, where X is $NR_1$, may be prepared by any one of the classical processes known for the preparation of 2-imidazolines; Ferm and Riebsomer, Chem. Rev. 593 (1954).

For example, treating a diamine of the formula V or its salt 1) with a carboxylic acid of the formula R—COOH, its ester, acid chloride, anhydride, amide, thioamide or nitrile derivative followed by ring closure.

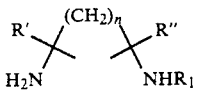

(wherein R, R', R", R1 and n are as defined above)

The reaction may be carried out in a solvent such as benzene at 130°–230° C. with azeotropic removal of water, Riebsomer, J. Amer. Chem. Soc. 70, 1629 (1948); Harnsberger and Riebsomer, J. Hetero. Chem. 1,188 (1964). The monoacyl or diacyl derivatives formed may or may not be isolated and ring closed, for example, in presence of oxides of calcium or magnesium or other dehydrating agents, Chitwood and Ried, J. Amer. Chem. Soc. 57,2424 (1935); Waldman and Chwala, Chem. Ber. 74,1763 (1941); Fr. Patent No. 811,423 (Apr. 14, 1937); C.A. 31,8550 (1937); Br. Patent No. 479,491 (Feb. 7, 1938); C.A. 32,5002 (1938); U.S. Pat. No. 2,155,877, (Apr. 23, 1939); and 2,155,878 (Apr. 25, 1939); C.A. 33,5878 (1939), Kyrides and Zienty, U.S. Pat. No. 2,404,300 (July 16, 1946); C.A. 40,6101 (1946); Kyrides, U.S. Pat. No. 2,404,299 (July 16, 1946); C.A. 41,160 (1946); Kyrides and Zienty, U.S. Pat. No. 2,399,601 (Apr. 30, 1946); C.A. 40,4180 (1946); Kyrides, U.S. Pat. No. 2,392,326 (Jan. 8, 1946); C.A. 40,1972 (1946); Aspinall, J. Amer. Chem. Soc. 61,3195 (1939); Hill and Aspinall, J. Amer. Chem. Soc. 61,822 (1939); Kyrides, J. Org. Chem. 12,577 (1947); Morill, U.S. Pat. No. 2,508,415 (May 23, 1950); C.A. 45,668 (1951); Piskov et. al., Khim. Geterotsikl. Soedin, 1112 (1976); C.A. 86,537h (1977). The nitrile derivative, R—CN, may be reacted with p-toluene sulfonate salt of diamine of formula V, Oxley and Short, J. Chem. Soc. 497 (1947), Savignac et. al., J. Hetero. Chem. 15,897 (1978) or with diamine of formula V in presence of catalytic amount of sulfur, Sawa, Nippon Kagaku Zasshi, 89,780 (1968); C.A. 70,19983q (1969) or in presence of catalytic amount of carbon disulfide at 80°–190° C. for 1 to 48 hours, Hueni, U.S. Pat. No. 2,868,802 (Jan. 13, 1959); Fruhstorfer and Muller-Calagan, Ger. Pat. 1,117,588 (Nov. 23, 1961); Hansen, Ger. Pat. 1,670,143 (May 30, 1974);

2) with the imidates of the formula

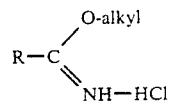

or amidines of the formula

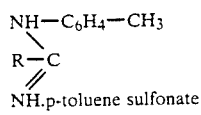

Bockmuhl and Knoll, U.S. Pat. No. 1,958,529 (May 15, 1934); C.A. 28,4539 (1934); Oxley and Short, J. Chem. Soc. 497 (1947); Short and Oxley, Brit. Patent, 614,032 (Dec. 8, 1948); C.A. 43,5049 (1949); I. G. Farbenindustrie A.G., Fr. Pat. 671,362 (Mar. 12, 1929).

The imidazolines may be prepared by treating the imidates mentioned above with an aminoalcohol, Drozdov and Bekhli, J. Gen. Chem. U.S.S.R. 14,480 (1944); C.A. 39,4590 (1945) or by heating a mixture of a carboxylic acid of the formula R—COOH and a 2-imidazolidone at 250°–300° C., I. G. Farbenindustrie A.G., Brit. Pat. 492,812 (Sept. 28, 1938); C.A. 33,1761 (1939).

2-Alkoxy-2-imidazolines may be prepared by the method of Kohn and Jung, J. Amer. Chem. Soc. 107, 2931 (1985) and 2-amino-2-imidazolines may be prepared, for example, by the method of Meschino and Bond, J. Org. Chem. 28, 3129 (1963).

Finally, 2-imidazolines may be prepared by reducing monoacyl derivatives of alpha aminonitriles in presence of a reducing agent, for example, Raney nickel, Hawkins and Biggs, J. Amer. Chem. Soc. 71,2530 (1949); Hawkins, U.S. Pat. No. 2,587,043 (Feb. 26, 1952); C.A. 46,9122 (1952).

N-substituted 2-imidazolines my be alternately prepared by alkylation of 2-substituted 2-imidazolines with an alkyl halide in presence of a strong base such as sodium hydride in hexamethylphosphotriamide (HMPT) or an organolithium compound, for example, butyllithium in an inert solvent according to Cognacq, British Patent No. 1,417,174 (Dec. 10, 1975).

The compounds of the present invention may be used as penetration enhancers in the same manner as described in my U.S. Pat. Nos. 3,989,816; 3,991,203; 4,415,563; 4,122,170; 4,316,893; 4,423,040; 4,424,210; 4,444,762 and U.S. application Ser. No. 783,621, and now U.S. Pat. No. 4,837,026 filed Sept. 30, 1985, and pending U.S. applications. Ser. No. 002,387, filed Jan. 12, 1987, Ser. No. 218,316, filed July 12, 1988, Ser. No. 07/345,457 filed May 1, 1989 and Ser. No. 07/348,387 filed May 8, 1989, which are hereby incorporated by reference.

The compounds of the present invention are useful as penetration enhancers for a wide range of physiologically active agents and the compositions disclosed herein are useful for topical and transdermal therapeutic effect of these agents. Typically systemically active agents which may be delivered transdermally are therapeutic agents which are sufficiently potent such that they can be delivered through the skin or other membranes to the bloodstream in sufficient quantities to produce the desired therapeutic effect. In general this includes agents in all of the major therapeutic areas including, but not limited to, anti-infectives, such as antibiotics and antiviral agents, analgesics, anorexics, anthelmintics, antiarthritics, antiasthma agents, anticonvulsants, antidepressants, antidiabetic agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, antiarryhthmics, antihypertensives, diuretics, vasodilators including general, coronary, peripheral and cerebral; central nervous system stimulants, cough and cold preparations, decongestants, diagnostics, hormones, hypnotics, immunosuppressives, muscle relaxants, parasympatholytics, parasympathomimetics, sedatives, tranquilizers and antiosteoporosis agents.

For topical applications the agents include antibiotics, fungistatic and fungicidal agents, corticosteroids, antiinflammatory agents, antiemetics, antipruritic agents, vasodilators, bronchodilators, expectorants, analgesics, antiosteoporosis agents, sunscreen compounds, antiacne agents, collagen softening agents and other similar compounds. Cosmetic agents, hair and skin dyes, natural and synthetic hormones, perfumes, insect repellents, diagnostic agents and other such compounds may also be advantageously formulated with these penetration enhancers.

Moreover, these penetration enhancers are useful in agriculture in the application of fertilizers, hormones, growth factors including micronutrients, insecticides, molluscicides, arachides, nematocides, rodenticides, herbicides, and other pesticides to plants, animals and pests. These penetration enhancers are also useful for penetration of micronutrients and chemical hybridization agents in seeds for enhanced plant growth. Of course, the appropriate dosage levels of all the physiologically active agents, without conjoint use of the penetration enhancing compounds of formula I, are known to those of ordinary skill in the art. These conventional dosage levels correspond to the upper range of dosage levels for compositions including a physiologically active agent and a compound of formula I as a penetration enhancer. However, because the delivery of the active agent is enhanced by compounds of the present invention, dosage levels significantly lower than conventional dosage levels may be used with success. Systemically active agents are used in amounts calculated to achieve and maintain therapeutic blood levels in a human or other animal over the period of time desired. (The term "Animal" as used here encompasses humans as well as other animals, including particularly pets and other domestic animals.) These amounts vary with the potency of each systemically active substance, the amount required for the desired therapeutic or other effect, the rate of elimination or breakdown of the substance by the body once it has entered the bloodstream and the amount of penetration enhancer in the formulation. In accordance with conventional prudent formulating practices, a dosage near the lower end of the useful range of a particular agent is usually employed initially and the dosage increased or decreased as indicated from the observed response, as in the routine procedure of the physician.

The present invention contemplates compositions of compounds of formula I, together with physiologically active agents from 0.05% to 100% of conventional dosage levels. The amount of compound of Formula I which may be used in the present invention is an effective, non-toxic amount for enhancing percutaneous absorption. Generally, for topical use the amount ranges between 0.01 to about 10 and preferably about 0.1 to 5 percent by weight of the composition. For transdermal enhancement of systemic agents, the amount of penetration enhancer which may be used in the invention varies from about 1 to 100 percent although adequate enhancement of penetration is generally found to occur in the range of about 1 to 30 percent by weight of the formulation to be delivered. For transdermal use, the penetration enhancers disclosed herein may be used in combination with the active agent or may be used separately as a pre-treatment of the skin or other body membranes through which the active agent is intended to be delivered.

Dosage forms for application to the skin or other membranes of humans and animals include creams, lotions, gels, ointments, suppositories, sprays, aerosols, buccal and sublingual tablets and any one of a variety of transdermal devices for use in the continuous administration of systemically active drugs by absorption through the skin, oral mucosa or other membranes, see for example, one or more of U.S. Pat. Nos. 3,598,122; 3,598,123; 3,731,683; 3,742,951; 3,814,097; 3,921,636; 3,972,995; 3,993,072; 3,993,073; 3,996,934; 4,031,894; 4,060,084; 4,069,307; r,201,211; 4,230,105; 4,292,299 and 4,292,303. U.S. Pat. No. 4,077,407 and the foregoing patents also disclose a variety of specific systemically active agents which may also be useful as in transdermal delivery, which disclosures are hereby incorporated herein by this reference.

The penetration enhancers of this invention may also be used in admixture with other penetration enhancers disclosed earlier and incorporated herein by reference.

Typical inert carriers which may be included in the foregoing dosage forms include conventional formulating materials, such as, for example, water, ethanol, 2-propanol, 1,2-propanediol, 1,3-butanediol, 1,2,3,-propanetriol, propanone, butanone, carboxylic acid esters such as isopropyl myristate, diisopropyl adipate and diisopropyl sebacate, acyclic and cyclic amides including N-methyl pyrrolidone, urea, freons, PEG- 200, PEG-400, Polyvinyl pyrrolidone, fragrances, gel producing materials such as "Carbopol", stearyl alcohol, stearic acid, spermaceti, sorbitan monooleate, sorbital, "polysorbates", "Tweens", methyl cellulose etc.

It will be readily appreciated by those skilled in the art that certain compounds represented by formula I exhibit chirality. However, where no designation of isomers is specified with respect to the compounds of this invention, it is to be understood that all possible stereoisomers are included.

It will also be readily appreciated by those skilled in the art that certain of the compounds described in the disclosure may form salts with carboxylic and mineral acids and it is understood that all such salts are included in the invention.

The examples which follow illustrate the penetration enhancers and the compositions of the present invention. However, it is understood that the examples are intended only as illustrative and are not to be construed as in any way limiting to scope of this invention.

EXAMPLE 1

Preparation of 2-undecyl-2-oxazoline

The reaction was carried out under nitrogen atmosphere in a three neck flask equipped with a magnetic stirring bar, reflux condenser, addition funnel and thermometer. 50 ml of 1-butanol and 667 mg (2.5 mmoles) of cadmium acetate dihydrate was introduced and the catalyst was dissolved by slight warming. 18.13 g (100 mmoles) of undecyl cyanide was added and the solution was heated to 125° C. 7.33 g (120 mmoles) of 2-aminoethanol was then added dropwise controlling the evolution of ammonia. At the end of the reaction (ca. 48 hrs.) the solvent was removed under vacuo. The residue was treated with 100 ml of petroleum ether and filtered after keeping for several hours. The filtrate was washed with water, dried over anhydrous magnesium sulfate, concentrated and the residue was distilled 114° C./0.5 mm to give 19.83 g (88%) of 2-undecyl-2-oxazoline.

EXAMPLE 2

Preparation of 2-decyl-2-oxazoline

Undecyl cyanide in Example 1 was substituted with 18.13 g (108.4 mmoles) of undecanenitrile and allowed to react with 7.5 ml (121.3) mmoles of aminoethanol in presence of cadmium acetate dihydrate (667 mg; 2.5 mmoles) in 1-butanol under identical reaction conditions. The reaction mixture was worked up following Example 1 and the residue was distilled at 118°-120° C./1.2 mm to give 14.72 g (64.3%) of 2-decyl-2-oxazoline.

EXAMPLE 3

Preparation of 2-heptadecyl-2-oxazoline

Undecyl cyanide in Example 1 was substituted with 26.55 g (100 mmoles) of heptadecyl cyanide and the reaction was repeated under identical conditions. The residue, after removal of 1-butanol under vacuo, was extracted with 150 ml of toluene at 70° C. and filtered. The filtrate was washed with water, dried, concentrated and the residue on slight wash with acetonitrile gave 23.79 g (77%) of 2-heptadecyl-2-oxazoline, m.p. 52°-53° C.

EXAMPLE 4

Preparation of 2-pentyl-2-oxazoline 9.72 g (100 mmoles) of hexanenitrile was substituted for undecyl cyanide in Example 1 and the reaction was repeated with 6.11 g (100 mmoles) of ethanolamine and 549 mg (2.5 mmoles) of zinc acetate dihydrate under identical conditions. At the end of the reaction the product was worked up as before and distilled at 73° C./10 mm to give 8.2 g (60%) of 2-pentyl-2-oxazoline.

EXAMPLE 5

Preparation of 4-methyl-2-undecyl-2-oxazoline 10.9 g (60 mmoles) of undecyl cyanide was treated with 5 g (66.6 mmoles) of DL-2-amino-1-propanol in presence of 400 mg (1.5 mmoles) of cadmium acetate dihydrate in 1-butanol as outlined under Example 1. 13.2 g (92%) of product was obtained on distillation at 115°-117° C./1-1.5 mm Hg.

EXAMPLE 6

The following compounds are prepared analogously following Example 5 and substituting DL-2-amino-1-propanol by 66.6 mmoles of the appropriate aminoalcohol.
4-Trifluoromethyl-2-undecyl-2-oxazoline
4-Isopropyl-2-undecyl-2-oxazoline
4-t-Butyl-2-undecyl-2-oxazoline

EXAMPLE 7

Preparation of 4-ethyl-2-undecyl-2-oxazoline 25 g (137.9 mmoles) of undecyl cyanide was treated with 15.2 ml (165 mmoles) of DL-2-amino-1-butanol in presence of 919 mg (3.54 mmoles) of cadmium acetate dihydrate in 1-butanol as outlined under Example 1. 31.31 g (89.6%) of product was obtained on distillation at 124°-125° C./1.2-1.4 mm Hg.

EXAMPLE 8

Preparation of 4,4-dimethyl-2-undecyl-2-oxazoline 64 g (320 mmoles) of dodecanoic acid and 61.1 ml (640 mmoles) of 2-amino-2-methylpropanol was placed in a two neck flask equipped with a vigreux column, distillation condenser and a thermometer. The temperature of the reaction mixture was slowly brought to 180° C. and maintained there for 9 hours. After cooling, a 10% alcoholic KOH solution (2 g, 3.6 mmoles) was added and the reflux was continued at 180° C. for 4 hours. The excess 2-amino-2-methylpropanol was distilled at aspirator pressure (86° C./18 mm). When the vapor temperature reached 103° C., the distillation was discontinued and the residue was taken in petroleum ether and filtered. The filtrate was washed with dilute KOH, water, dried and concentrated. The oil was distilled at 120° C./1.2 mm Hg to give 70.5 g (87%) of product.

EXAMPLE 9

Preparation of 4,4-dimethyl-2-pentyl-2-oxazoline

Following the procedure under Example 8, 6.085 g (52.4 mmoles) of hexanoic acid and 10 ml (9.34 g, 104.8 mmoles) of 2-amino-2-methylpropanol were heated to 185° C. Work up and fractional distillation gave 7.2 g (81%) of product, b.p. 90°-92° C./25 mm Hg.

EXAMPLE 10

Preparation of 4,4-dimethyl-2-heptadecyl-2-oxazoline

Following example 8, 14.9 g (52.4 mmoles) of octadecanoic acid and 9.34 g (104.8 mmoles) of 2-amino-2-methylpropanol gave 14.1 g (79.7%) of product, b.p. 140°–143° C./0.01 mm Hg.

EXAMPLE 11

Preparation of 4,4-Dimethyl-2-(1-dodecen-2-yl)2-oxazoline 4.2 g (141 mmoles) of paraformaldehyde was added to 22.5 g (88.8 mmoles) of 4,4-dimethyl-2-undecyl-2-oxazoline (obtained in Example 8) at 90° C. The mixture was stirred at 90° C. for 30 minutes and the temperature was raised by 5° C. increment every half hour up to 115° C. 20 ml of cumene was added and the mixture was refluxed for 2.5 hours at 180° C. with removal of water using a Dean-Stark trap. The solution was distilled at 126°–129° C./1 mm to give 18.2 g of product. This contained 5–10% of starting oxazoline. LPLC purification on 40–60 micron silica gel (petroleum ether to 90% petroleum ether-ethyl acetate gradient) gave 16.5 g (70%) of pure product.

EXAMPLE 12

The following compounds are prepared analogously following Example 11 and substituting the 4,4-dimethyl-2-undecyl-2-oxazoline by equimolar amounts of the corresponding 4-trifluoromethyl and 4-methyl-4-trifluoromethyl derivatives.
4-Trifluoromethyl-2-(1-dodecen-2-yl)-2-oxazoline
4-Methyl-4-trifluoromethyl-2-(1-dodecen-2-yl-2-oxazoline

EXAMPLE 13

Preparation of 4-hydroxymethyl-4-methyl-2-undecyl-2-oxazoline

A mixture of 20.03 g (100 mmoles) of dodecanoic acid and 11.57 g (110) mmoles) of 2-amino-2-methyl-1,3-propanediol in 10 ml of xylene was heated for 30 hours at 185°–190° C. with azeotropic removal of water. The reaction mixture was taken up in ethyl acetate and was washed with water to remove excess amino alcohol. The organic layer was dried, concentrated and the residue was distilled at 152°–155° C./1 mm Hg to give 22.8 g (84.6%) of 4-hydroxymethyl-4-methyl-2-undecyl-2-oxazoline.

EXAMPLE 14

Preparation of 4-hydroxymethyl-4-ethyl-2-undecyl-2-oxazoline 26 g (130 mmoles) of dodecanoic acid and 31 g (260 mmoles) of 2-amino-2-ethyl-1,3-propanediol were condensed together by heating at 185°–190° C. for 30 hours. Work up and distillation of the residue at 160°–162° C./1 mm Hg gave 33.19 g (90%) of the product.

EXAMPLE 15

Preparation of 2-(2-dodecyl)-2-oxazoline 100 mmoles of 2-cyanododecane is treated with 120 mmoles of 2-aminoethanol in 50 ml of 1-butanol in presence of 2.5 mmoles of cadmium acetate dihydrate as outlined under Example 1 to give 2-(2-dodecyl)-2-oxazoline.

EXAMPLE 16

The following compounds are prepared analogously following Example 15 and substituting 2-aminoethanol by 120 mmoles of the appropriate 2-aminoalkanol derivative.
4-Methyl-2-(2-dodecyl)-2-oxazoline
4-Isopropyl-2-(2-dodecyl)-2-oxazoline
4-t-Butyl-2-(2-dodecyl)-2-oxazoline
4-Trifluoromethyl-2-(2-dodecyl)-2-oxazoline

EXAMPLE 17

Preparation of 2-(2-Methyl-2-decyl)-2-oxazoline 100 mmoles of 2-cyano-2-methyldodecane is reacted with 120 mmoles of 2-aminoethanol in 50 ml of 1-butanol in presence of 2.5 mmoles of cadmium acetate dihydrate as outlined under Example 1 to give 2-(2-methyl-2-decyl)-2-oxazoline.

EXAMPLE 18

The following compounds are prepared analogously following Example 17 and substituting 2-aminoethanol by 120 mmoles of the appropriate 2-aminoalkanol derivative.
4-Methyl-2-(2-methyl-2-decyl)-2-oxazoline
4-Isopropyl-2-(2-methyl-2-decyl)-2-oxazoline
4-Trifluormethyl-2-(2-methyl-2-decyl)-2-oxazoline

EXAMPLE 19

Preparation of 4,4-Dimethyl-2-(2-dodecyl)-2-oxazoline 10 g of 4,4-Dimethyl-2-(1-dodecen-2-yl)-2-oxazoline, obtained in Example 11, was dissolved in 200 ml ethanol and hydrogenated in a Parr apparatus over 1 g of 10% Pd/C at 50 p.s.i. The catalyst was removed and the filtrate was concentrated to give the product. This was distilled at 120°–122° C./0.8 mm to give 9.68 g (96.5%) of colorless product.

EXAMPLE 20

Preparation of 4,4-Dimethyl-2-(2-methyl-3-tridecyl)-2-oxazoline

A solution of 25.34 g (100 mmoles) of 4,4-dimethyl-2-undecyl-2-oxazoline in 250 ml of dry THF under nitrogen atmosphere was cooled to −78° C. To this was added 62.5 ml (100 mmoles) of 1.6M solution of n-butyl lithium in hexane over a period of 15 minutes and the solution was further stirred for 2 hours. 18.45 g (150 mmoles) of 2-bromopropane was added at −78° C. over a period of 30 minutes and the resulting solution was allowed to warm to room temperature overnight. The solution was poured into 250 ml of saturated ammonium chloride solution and the organic phase was separated. The aqueous phase was extracted with 2×100 ml of ether, the organic phases were combined and extracted with 2×200 ml of brine. After drying over anhydrous magnesium sulphate, the solution was concentrated and the residue was distilled at reduced pressure. 10.2 g of starting material was recovered. 8.82 g (50% based on recovered starting material) of product distilled at 131°–134° C./0.8 mm Hg. 2.98 g (14.8%) of disubstituted product was obtained as a higher boiling fraction.

EXAMPLE 21

Preparation of 4-Decyl-2-trifluoromethyl-2-oxazoline

To a cooled solution of 10.2 g of 2-amino-1-dodecanol and 15 ml of triethylamine in 100 ml of dichloromethane was slowly added a solution of 7.1 ml of trifluoroacetic anhydride in 30 ml of dichloromethane. After 3 hours at room temperature the reaction mixture was poured into sodium bicarbonate solution and then extracted with ether. The organic phase was dried, concentrated and the residual oil was heated at 160°–180° C. for 12 hours. The dark oil was dissolved in hexane and was washed with sodium bicarbonate solution and water. The hexane phase was dried, concentrated and the residual oil was distilled at 100°–110° C. at 0.1 mm to give 10.4 g (73.6%) of a clear oil.

EXAMPLE 22

Preparation of 2-Undecyl-2-imidazoline 18.32 g (100 mmoles) of undecyl cyanide, 8.5 ml (127 mmole) of ethylenediamine and 0.5 ml of carbon disulfide were mixed and heated in an oil bath at 125° C. for 24 hours. The reaction mixture was cooled, treated with dilute hydrochloric acid and treated with charcoal. The light yellow filtrate was basified and extracted with ethyl acetate, the organic extracts dried over magnesium sulfate and concentrated. The residue was Kugelrohr distilled and then recrystallized from toluene. Yield 13.7 g (61.1%), m.p. 82° C.

EXAMPLE 23

Preparation of 1-Methyl-2-heptyl-2-imidazoline 14.207 g (113.46 mmoles) of heptyl cyanide, 10.726 g (144.69 mmoles) of N-methylethylenediamine and 0.5 ml of carbon disulfide were mixed and heated at 125° C. for 24 hours. The solution was cooled, diluted with ethyl acetate and extracted with dilute hydrochloric acid. The acidic solution was basified with sodium hydroxide and extracted with ethyl acetate. The organic extracts were treated with charcoal, filtered, concentrated and Kugelrohr distilled at 105° C./1.2 mm to give 19.73 g (77.3%) of the product.

EXAMPLE 24

Preparation of 1-(2-Hydroxyethyl)-2-octyl-2-imidazoline 13.02 g (93.51 mmoles) of octyl cyanide was treated with 12.327 g (118.36 mmoles) of 2-(2-aminoethylamino)ethanol in presence of 0.5 ml of carbon disulfide at 125° C. for 24 hrs. and worked up as outlined under Example 23. Distillation of the residue at 167°–169° C./0.5 mm gave 12.332 g (62.7%) of product.

EXAMPLE 25

Preparation of 1-(2-Hydroxyethyl)-2-undecyl-2-imidazoline 58.7 g (564.4 mmoles) of 2-(2-aminoethylamino)ethanol and 122.8 g (538.6 mmoles) of ethyl dodecanoate were heated at 125° C. and ethanol was removed by distillation. 100 ml of toluene was cautiously added and water was removed azeotropically on further reflux. The reaction mixture was fractionally distilled to give 100.2 g (69.5%) of pure product, m.p. 40°–42° C.

EXAMPLE 26

Preparation of 1-(4-Hydroxybutyl)-2-undecyl-2-imidazoline 8 g (60.6 mmoles) of 4-(2-aminoethylamino)butanol and 12.5 g of ethyl dodecanoate were treated as under Example 25. The resulting 10.8 g of an oil (66.7%) was dissolved in 100 ml of hexane and kept in the freezer to give 8.8 g of pure product, m.p. 58°–60° C.

EXAMPLE 27

Preparation of 1-(2-Ethoxyethyl)-2-undecyl-2-imidazoline 2.54 g (19.2 mmoles) of N-(2-ethoxyethyl)ethylenediamine and 4.3 g of ethyl dodecanoate were treated as under Example 25. Distillation of the crude product at 128°–130° C./0.2 mm gave 2.9 g (52%) of product.

1-(2-methoxyethyl)-2-undecyl-2-imidazoline was similarly prepared from 30.8 g of ethyl dodecanoate and 16 g of N-(2-methoxyethyl)ethylenediamine. Distillation of the crude product at 150° C./0.1 mm gave 9.3 g of pure product.

EXAMPLE 28

Preparation of 1-Isopropyl-2-undecyl-2-imidazoline 18.324 g of Undecyl cyanide, 15.12 g of N-isopropylethylenediamine and 0.5 ml of carbon disulfide were heated at 125° C. for 24 hrs. and worked up as mentioned under Example 23, followed by distillation at 150° C./1.2 mm gave 21.93 g (82.3%) of the product.

EXAMPLE 29

Preparation of 4-Methyl-2-undecyl-2-imidazoline 18.13 g (100 mmoles) of undecyl cyanide, 9.3 g (125 mmoles) of 1,2-diaminopropane and 0.5 ml of carbon disulfide were heated to 125° C. for 24 hrs. and then worked up as mentioned under Example 23. Kugelrohr distillation at 163°–165° C./1.2–1.4 mm Hg gave 17.85 g (75%) of product.

EXAMPLE 30

Preparation of 4,4-Dimethyl-2-undecyl-2-imidazoline 18.31 g (100 mmoles) of undecyl cyanide, 11 g (125 mmoles) of 1,2-diamino-2-methylpropane and 0.5 ml of carbon disulfide were heated at 125° C. for 24 hrs. and then worked up as under Example 23. Distillation at reduced pressure gave 19.66 g (78%) of the product.

EXAMPLE 31

Preparation of 4,4-Dimethyl-2-pentyl-2-imidazoline 8.41 g (95.4 mmoles) of 1,2-diamino-2-methylpropane, 7.4 g (76.16 mmoles) of hexanenitrile and 0.4 ml of carbon disulfide were heated at 125° C. for 24 hours and then worked up as under Example 23. Distillation at 105°–107° C./0.5 mm gave 9.4 g (73.4%) of product.

EXAMPLE 32

Preparation of 4-Methyl-4-t-butyl-2-undecyl-2-imidazoline 15 g of 2-cyano-2-decanoylamino-3,3-dimethylbutane (prepared from acylation of aminonitrile obtained from treatment of pinacolone with sodium cyanide and ammonium chloride) in 250 ml of 95% ethanol and 70 ml of ammonium hydroxide was hydrogenated with T-1 Raney Nickel. The catalyst was filtered off. The filtrate was concentrated and the residue was distilled at reduced pressure to give 7.5 g (52%) of the product.

EXAMPLE 33

Preparation of
4,4-Dimethyl-1-isopropyl-2-undecyl-2-imidazoline 22.84 g. (100 mmoles) of ethyl dodecanoate and 15.34 g. (118 mmoles) of $N_1$-isopropyl-2-methyl-1,2-propanediamine was heated at 130°-230° C. until approximately 100 mmoles of ethanol was collected. Toluene was then cautiously added and the heating was continued until no more water separated. The solution was acidified, the aqueous layer was separated and basified with NaOH. This was extracted with ethyl acetate, the organic extract was dried and concentrated. The oil was distilled at 150°-152° C./1.2 mm to give 16.74 g (58%) of product.

EXAMPLE 34

The following compounds were prepared following the procedure in Example 33 and substituting the $N_1$-isopropyl-2-methyl-1,2-propanediamine by equimolar amount of the appropriately $N_1$-substituted ethylenediamine.

A) 1-Methyl-2-undecyl-2-imidazoline 131°-133° C./1 mm 79% yield

B) 1-Propyl-2-undecyl-2-imidazoline 160° C./36 1 mm 76.36% yield

EXAMPLE 35

Preparation of
1-(2-Carbmethoxyethyl)-2-undecyl-2-imidazoline 2.2 g (9.82 mmoles) of 2-undecyl-2-imidazoline and 1.4 g (16.3 mmoles) of methyl acrylate were dissolved in 50 ml of methylene chloride and the solution was heated to reflux. The reaction was followed by glc. The solution was concentrated and the residue was distilled at 160°-170° C./0.1 mm to give 2.2 g (72.4%) of product.

EXAMPLE 36

Preparation of
1-[2-(2-Hydroxyethoxy)ethyl]-2-undecyl-2-imidazoline 13.7 g (92.6 mmoles) N-[2-(2-Hydroxyethoxy)ethyl]ethylenediamine and 19.6 g (86 mmoles) of ethyl dodecanoate were mixed and heated in a flask equipped with a Dean-Stark trap. After the separated ethanol and water were distilled off, the residue was kugelrohr distilled at 160°-170° C./0.1 mm to give 13.6 g (50.7%) of crude product. Recrystallization from ethyl acetate/hexane gave white crystalline material, m.p. 58°-60° C.

EXAMPLE 37

Preparation of
1-(2-Hyrdoxyethyl)-2-undecyl-2-imidazoline acetate 34 g (127 mmoles) 1-(2-Hyrdoxyethyl)-2-undecyl-2-imidazoline was dissolved in 300 ml of hexane and 8.5 g (14.2 mmoles) of acetic acid in 50 ml of hexane were reacted. The precipitate was filtered and then dried at 40°-50° C. under high vacuum for 5 hours. Yield 40.7 g (97.8%). The compound was hydroscopic and was hydrated to a gel upon absorbing moisture.

EXAMPLE 38

Preparation of
4,4-Dimethyl-1-n-butyl-2-undecyl-2-imidazoline 22 ml (55 mmoles) of a 2.5M solution of butyl lithium in hexane are added to 12.62 g (50 mmoles) of 4,4-dimethyl-2-undecyl-2-imidazoline in 50 ml of anhydrous benzene at a temperature kept at around 20° C. The mixture is then stirred for 2 hours at ambient temperature (15° to 20° C.). 8.22 g (60 mmoles) of 1-bromobutane is then added dropwise to the reaction mixture, keeping the temperature at around 20° C. The reaction mixture is then stirred at ambient temperature until it is homogenous, after which it is refluxed for 3 hours. After cooling, 50 ml of water is added, the mixture is stirred for half hour, decanted and extracted with 100 ml of ether. After drying over magnesium sulfate the solvent is removed in vacuo and the oil is distilled at reduced pressure to give 10.34 g (67%) of the product.

The compounds of the present invention were tested in vitro as penetration enhancers according to the procedure outlined below. The penetration enhancers were formulated with pharmacologically active agents in creams and patches. Permeation of the active agent through human stratum corneum in vitro over a specific study period was compared to control formulation without enhancer. Higher permeation of the active agent in the presence of an enhancer exemplified the invention.

EXAMPLE 39

Human stratum corneum was isolated from full thickness human skin as described by Bronaugh et. al., J. Pharm. Sci. 75, 1094 (1986). The skin was placed between the donor and the receptor compartments of diffusion cells in such a way that the dermal side of the skin faced the receptor compartment which was filled with normal saline (pH 7.2-7.4) or appropriate releasing media. The stratum corneum was equilibrated at 37° C. overnight prior to the application of a topical formulation or a transdermal patch. All formulations were studied in triplicate.

About 500 mg of the following four isosobide dinitrate (ISDN) cream formulations (40% ISDN & 60% Lactose) were applied to cover the stratum corneum surface within the donor compartment. The entire contents of the receptor compartment were removed at specific time intervals for duration of the study period and replenished with fresh saline. The aliquots were analyzed by HPLC and the average cumulative amount of ISDN in micrograms permeating over the study period was calculated. The results are shown below.

| Cream Formulation | Average Cumulative Amount of ISDN in Micrograms Permeating over 24 hours |
| --- | --- |
| (1) 0.7% ISDN (Control) | 442.5 ± 27.7 |
| (2) 0.7% ISDN + 1% Enhancer of Example 30 | 566.1 ± 119 |
| (3) 0.7% ISDN + 1% Enhancer of Example 34 A | 861.8 ± 158.3 |
| (4) 0.7% ISDN + 1% Enhancer of Example 34 B | 747.8 ± 135.8 |

The results clearly indicated that the formulations containing Enhancers of Examples 30, 34 A and 34 B showed superior permeation for Isosorbide Dinitrate as compared to control.

EXAMPLE 40

Procedure of Example 39 was repeated with the following Isosorbide Dinitrate (ISDN) cream formulations.

| Cream Formulation | Average Cumulative Amount of ISDN in Micrograms Permeating over 48 Hours |
|---|---|
| (1) 0.7% ISDN (Control) | 535.0 ± 25.0 |
| (2) 0.7% ISDN + 2% Enhancer of Example 25 | 872.3 ± 85.0 |

The results indicated that the formulation containing the Enhancer of Example 25 showed superior permeation for Isosorbide Dinitrate as compared to control.

EXAMPLE 41

Procedure of Example 39 was repeated with the following Isosorbide Dinitrate (ISDN) cream formulations.

| Cream Formulation | Average Cumulative Amount of ISDN in Micrograms Permeating over 51 Hours |
|---|---|
| (1) 1% ISDN (Control) | 678.5 ± 84.0 |
| (2) 1% ISDN + 2% Enhancer of Example 27 | 1255.3 ± 96.0 |

The results clearly indicated that the formulation containing the Enhancer of Example 27 shows superior permeation for Isosorbide Dinitrate as compared to control.

EXAMPLE 42

Procedure of Example 39 was repeated with the following Haloperidol Decanoate (HD) cream formulations. Normal saline in the receptor compartment was replaced by 2-propanol/saline (1:1).

| Cream Formulation | Average Cumulative Amount of HD in Micrograms Permeating over 51 Hours |
|---|---|
| (1) 5% HD (Control) | 617.68 ± 17.68 |
| (2) 5% HD + 3% Enhancer of Example 25 | 1209.00 ± 131.36 |
| (3) 5% HD + 3% Enhancer of Example 27 | 1829.20 ± 15.55 |

The results clearly indicated that the formulations containing Enhancers of Examples 25 and 27 showed superior permeation for Haloperidol Decanoate as compared to control.

EXAMPLE 43

Procedure of Example 39 was repeated with the following Nifedipine (NIF) cream and patch formulations. Normal saline in the receptor compartment was replaced by ethanol/saline (3:7).

| Cream Formulation | Average Cumulative Amount of NIF in Micrograms Permeating over 51 Hours |
|---|---|
| (1) 5% NIF (Control) | 157.9 ± 14.8 |
| (2) 5% NIF + 5% Enhancer of Example 25 | 545.5 ± 33.3 |
| Patch Formulation | |
| (1) 5% NIF (Control) | 3.0 ± 0.0 |
| (2) 5% NIF + Enhancer of Example 25 | 4.73 ± 1.2 |

The results clearly indicated that the cream and patch formulations containing the Enhancer of Example 25 showed superior permeation for Nifedipine as compared to control.

EXAMPLE 44

Procedure of Example 39 was repeated with the following Nicotine (NI) cream and patch formulations.

| Cream Formulation | Average Cumulative Amount of NI in Micrograms Permeating over 51 Hours |
|---|---|
| (1) 1% NI (Control) | 858.3 ± 73.0 |
| (2) 1% NI + 3% Enhancer of Example 25 | 1733.4 ± 76.0 |
| Patch Formulation | |
| (1) 5% NI (Control) | 151.7 ± 28.2 |
| (2) 5% NI + 1% Enhancer of Example 25 | 284.2 ± 20.5 |
| (3) 5% NI + 3% Enhancer of Example 25 | 302.3 ± 92.4 |
| (4) 5% NI + 5% Enhancer of Example 25 | 296.8 ± 25.1 |

The results clearly indicated that the cream and patch formulations containing the Enhancer of Example 25 showed superior permeation for Nicotine as compared to control.

EXAMPLE 45

Procedure of Example 39 was repeated with the following 17B-Estradiol (ES) patch formulations. Normal saline in the receptor compartment was replaced by ethanol/saline (3:7).

| Patch Formulation | Average Cumulative Amount of ES in Micrograms Permeating over 51 Hours |
|---|---|
| (1) 5% ES (Control) | 30.90 ± 1.00 |
| (2) 5% ES + 9% Enhancer of Example 27 | 151.00 ± 5.80 |

The results clearly indicated that the patch formulation containing the Enhancer of Example 27 showed superior permeation for 17B-Estradiol as compared to control.

EXAMPLE 46

Procedure of Example 39 was repeated with the following two sets of Progesterone (PG) patch formulations. Normal saline in the receptor compartment was replaced with ethanol/saline (3:7).

| Patch Formulation | Average Cumulative Amount of PG in Micrograms Permeating over 51 Hours |
|---|---|
| SET A | |
| (1) 3% PG (Control) | 176.3 ± 92.0 |
| (2) 3% PG + 5% Enhancer of Example 25 | 562.9 ± 25.0 |
| (3) 3% PG + 5% Enhancer 1-(2-Hydroxyethyl)-2-(heptadec-8-enyl)-2-imidazoline | 552.0 ± 31.0 |
| SET B | |
| (1) 3% PG (Control) | 25 ± 17 |
| (2) 3% PG + 1% Enhancer of Example 30 | 238 ± 44 |

The results clearly indicated that the patch formulations containing the Enhancers of Examples 25 and 30 and the Enhancer 1-(2-Hydroxyethyl)-2-(heptadec-8-enyl)-2-imidazoline showed superior permeation for Progesterone as compared to control.

EXAMPLE 47

Procedure of Example 39 was repeated with four different sets of Hydrocortisone (HC) cream formulations.

| Cream Formulation | Average Cumulative Amount of HC in Micrograms permeating over 24 Hours |
|---|---|
| SET A | |
| (1) 0.5% HC (Control) | 1.657 ± 0.205 |
| (2) 0.5% HC + 1% Enhancer of Example 24 | 6.364 ± 0.55 |
| (3) 0.5% HC + 1% Enhancer of Example 30 | 13.634 ± 7.68 |
| (4) 0.5% HC + 1% Enhancer of Example 34 A | 13.78 ± 2.91 |
| (5) 0.5% HC + 1% Enhancer of Example 34 B | 9.82 ± 3.18 |
| SET B | |
| (1) 0.5% HC, Commercial OTC (Control) | 5.02 ± 0.30 |
| (2) 0.5% HC, Commercial OTC + 1% Enhancer of Example 30 | 13.63 ± 7.68 |
| (3) 1% HC, Commercial Rx (Control) | 4.94 ± 0.10 |
| (4) 1% HC, Commercial Rx + 1% Enhancer of Example 30 | 26.10 ± 14.92 |
| SET C | |
| (1) 1% HC, Commercial Rx (Control) | 3.38 ± 1.39 |
| (2) 1% HC, Commercial Rx + 1% Enhancer of Example 30 | 8.45 ± 2.41 |
| (3) 2.5% HC, Commercial Rx | 3.22 ± 0.30 |
| SET D | Over 48 Hours |
| (1) 0.5% HC (Control) | 27.71 ± 1.84 |
| (2) 0.5% HC + 2% Enhancer of Example 25 | 67.53 ± 3.34 |

All four sets of studies indicated that the formulations containing Enhancers of Examples 24, 25, 30, 34 A and 34 B showed superior permeation for Hydrocortisone as compared to control.

EXAMPLE 48

Example 39 was repeated with 1% Diclofenac gel, with and without compound of Example 21, was evaluated. The aliquots were analyzed by U.V. Spectrophotometry and average cumulative amount of drug permeating over 24 hours was calculated. The results shown below demonstrate that the Compound of Example 21 increases the permeation of Diclofenac through human skin when compared to control.

| Gel Formulation | Average Cumulative Amount of Diclofenac in Micrograms permeating over 24 hours. |
|---|---|
| 1% Diclofenac (control) | 106.7 ± 33.5 |
| 1% Diclofenac + 1% Compound of Example 21 | 154.13 ± 0.01 |

EXAMPLE 49

The compounds of Examples 8 and 13 were tested as penetration enhancing agents according to the procedure below:

Skin from female hairless mice, 8-12 weeks old, was removed from the animals and placed between the donor and the receptor compartments of diffusion cells, with normal saline (pH 7.2–7.4) bathing corium. The skin was incubated at 37° C. and the ambient humidity.

100 microliters of the solution containing 1 mg of test drug was applied to the epidermal surface within the donor compartment. The entire contents from the 4.2 ml receptor compartment bathing the corium were removed for analysis at 5 or 6, 12 and 24 hours intervals. In each case, the receptor compartment was refilled with 4.2 ml of fresh normal saline.

The aliquots removed after 5 or 6, 12 and 24 hours were analyzed by HPLC using a C-18 reverse phase column. The test solutions used in this experiment contained 1% Hydrocortisone, 2% 1,2-propanediol and 2% penetration enhancer. The control solution did not have penetration enhancer.

The results, as reported in Table 1 below, are average for two cells and clearly show that the compounds of Examples 8 and 13 have far superior penetration enhancing properties as compared to the control.

TABLE 1

| | | % Penetration | | |
|---|---|---|---|---|
| Penetration Enhancer | hrs. 5 | 6 | 12 | 24 |
| (1) Compound of Example 8 | — | 16.1 | 28.2 | 49.1 |
| (2) Compound of Example 13 | — | 8.8 | 17.3 | 34.9 |
| (3) Control | — | 1.3 | 1.8 | 2.4 |

EXAMPLE 50

The compounds of Examples 8 was tested as penetration enhancers according to the procedure outlined under Example 49. 1% hydrocortisone in the formulations of Example 49 was substituted by 1% 5-Fluorouracil. The results are outlined in Table 2 and clearly show that the compound of Example 8 is superior to the control.

TABLE 2

| | | % Penetration | |
|---|---|---|---|
| Penetration enhancer | hrs 6 | 12 | 24 |
| (1) Compound of Example 8 | 59.2 | 60.3 | 60.5 |
| (2) Control | 8.7 | 10.4 | 10.9 |

EXAMPLE 51

The following formulation is prepared.

| | Solution % |
|---|---|
| Griseofulvin | 1 |
| 4-Decyl-2-trifluoromethyl-2-oxazoline | 1 |
| C12–C15 benzoate | 5 |
| Fragrance | 0.1 |
| Ethanol | 92.9 |

This formulation is effective in the treatment of fungus infection.

EXAMPLE 52

An aerosol form of the formulation of Example 51 is prepared by preparing the following mixture:

| | |
|---|---|
| Formulation | 25% |
| Freon* | 75% |

*Freon is 75/25 Freon 114/12

EXAMPLE 53

The following cream formulation is prepared:

|  | % |
| --- | --- |
| Clindamycin Base | 1.0 |
| Stearyl alcohol, U.S.P. | 12.0 |
| Ethoxylated cholesterol | 0.4 |
| Synthetic spermaceti | 7.5 |
| Sorbitan monooleate | 1.0 |
| Polysorbate 80, U.S.P. | 3.0 |
| 4-Decyl-2-trifluoromethyl-2-oxazoline | 0.9 |
| Sorbitol solution, U.S.P. | 5.5 |
| Sodium citrate | 0.5 |
| Chemoderm #844 | 0.2 |
| Purified water | 68.0 |

This formulation is effective in the treatment of acne.

EXAMPLE 54

The following solution formulations are prepared:

|  | A (%) | B (%) |
| --- | --- | --- |
| Clindamycin base | — | 1.0 |
| Clindamycin phosphate acid | 1.3 | — |
| Sodium hydroxide | 0.077 | — |
| 1 M Hydrochloric acid | — | 2.27 |
| Disodium edentate.2H2O | 0.003 | 0.003 |
| Fragrances | 0.5 | 0.5 |
| 4-Decyl-2-trifluoromethyl 2-oxazoline | 1.0 | 1.0 |
| Purified water | 20.0 | 17.73 |
| Isopropanol | 77.12 | 77.497 |

These solutions are effective for the treatment of acne in humans.

EXAMPLE 55

The following solution formulation is prepared:

|  | % |
| --- | --- |
| Neomycin sulfate | 0.5 |
| Lidocaine | 0.5 |
| Hydrocortisone | 0.25 |
| 4-Decyl-2-trifluoromethyl-2-oxazoline | 1.0 |
| Propylene glycol | 97.75 |

This solution is effective for the treatment of otitis in domestic animals.

EXAMPLE 56

The following sunscreen emulsion is prepared:

|  | % |
| --- | --- |
| PABA | 2.0 |
| Benzyl alcohol | 0.5 |
| 4-Decyl-2-trifluoromethyl-2-oxazoline | 1.0 |
| Polyethylene glycol | 10.0 |
| Isopropyl lanolate | 3.0 |
| Lantrol | 1.0 |
| Acetylated lanolin | 0.5 |
| C12-C15 benzoate | 5.0 |
| Diisopropyl adipate | 2.0 |
| Cetyl alcohol | 1.0 |
| Veegum | 1.0 |
| Propylene glycol | 3.0 |

-continued

|  | % |
| --- | --- |
| Purified water | 70.0 |

EXAMPLE 57

The following antineoplastic solution is prepared:

|  | % |
| --- | --- |
| 5-Fluorouracil | 5 |
| 4-Decyl-2-trifluoromethyl-2-oxazoline | 1.5 |
| Polyethylene glycol | 5 |
| Purified water | 88.5 |

EXAMPLE 58

The following insect repellant atomizing spray is prepared:

|  | % |
| --- | --- |
| N,N-diethyltoluamide | 0.5 |
| 4-Decyl-2-trifluoromethyl-2-oxazoline | 0.5 |
| Ethanol | 99 |

EXAMPLE 59

The following cream formulation may be prepared containing about 0.001 to 1 percent, with preferably 0.1% fluocinolone acetonide:

|  | % |
| --- | --- |
| Oil Phase |  |
| Fluocinolone acetonide | 0.1 |
| 4-Decyl-2-trifluoromethyl 2-oxazoline | 1.6 |
| Cetyl alcohol | 9.3 |
| Stearyl alcohol | 1.3 |
| Glyceryl monostearate | 3.8 |
| Water Phase |  |
| Propylene glycol | 10 |
| Sodium dodecyl sulfate | 0.1 |
| Deionized water q.s. | 100 |

The steriod is dissolved in the vehicle and added to a stirred, cooling melt of the ingredients. The preparation is particularly useful for the treatment of inflamed dermatoses by topical application to the affected skin area. The amount and frequency of application is in accordance with standard practice for topical application of this steroid. Penetration of this steroid in the inflamed tissue is enhanced and a therapeutic level is achieved more rapidly and sustained for longer duration than when the steroid is applied in the conventional formulation.

EXAMPLE 60

The following analgesic gel is prepared:

|  | % |
| --- | --- |
| Carbopol 941 | 1.5 |
| Diclofenac | 1 |
| Ethanol | 35 |
| Diisopropanolamine | 1.8 |
| Diisopropyl adipate | 5 |

| | % |
|---|---|
| 4-Decyl-2-trifluoromethyl-2-oxazoline | 2 |
| Water | 53.7 |

EXAMPLE 61

The following cream formulation is prepared:

| | % |
|---|---|
| Isosorbide dinitrate | 10.0 |
| Glycerol monostearate | 5.5 |
| Polyoxyethylene stearate | 4.5 |
| C8–C18 fatty acid esters of a glycerol ethoxylated with about 7 moles of ethylene oxide | 8 |
| 4-Decyl-2-trifluoromethyl-2-oxazoline | 2 |
| Sorbic acid | 0.165 |
| Ascorbyl palmitate | 0.055 |
| Citric acid | 0.1 |
| Na EDTA | 0.014 |
| Fragrance | 0.05 |
| Water | 69.616 |

This formulation is effective in the treatment of angina.

EXAMPLE 62

The following skin moisturizing formulation is prepared:

| | % |
|---|---|
| Pyrrolidonecarboxylic acid Na | 1 |
| Glycerine | 4 |
| Citric acid | 0.03 |
| Sodium citrate | 0.05 |
| Allantoin | 0.1 |
| Ethanol, 95% | 9 |
| Oleth-15 | 1 |
| Linoleic acid | 1 |
| 4-Decyl-2-trifluoromethyl-2-oxazoline | 2 |
| Sunscreen agent | 0.1 |
| Water | 81.72 |

EXAMPLE 63

Example 39 is repeated, except the Isosorbide Dinitrate is substituted by 0.5–10% amount by weight of each of the following therapeutically active agents.

| % | |
|---|---|
| 1–10 | Indomethacin |
| 1–10 | Diclofenac |
| 1–10 | Piroxicam |
| 1–10 | Propranolol |
| 0.5–5 | Fentanyl |
| 0.5–5 | Naloxone |
| 0.5–5 | Hydromorphone |
| 1–10 | Diltiazem |
| 1–10 | Nicardipine |
| 1–10 | Albuterol |
| 1–10 | Metaproterenol |
| 0.1–3 | Clonidine |
| 0.1–3 | 5-Fluorouracil |
| 0.5–5 | Acyclovir |
| 0.1–3 | Alprazolam |
| 0.5–5 | Lisinopril |
| 0.5–5 | Clindamycin |
| 1–10 | Clotrimazole |
| 1–10 | Miconazole |
| 1–10 | Griseofulvin |

Comparable results are obtained.

EXAMPLE 64

Examples 51–62 are repeated, except the 4-Decyl-2-trifluoromethyl-2-oxazoline is replaced with an equal amount of each of the following listed compounds, and comparable results are obtained.
4-trifluoromethyl-2-undecyl-2-oxazoline
4-Methyl-4-trifluoromethyl-2-undecyl-2-oxazoline
4,4-Dimethyl-2-(1-dodecen-2-yl)-2-oxazoline
4-t-Butyl-2-(dodecyl)-2-oxazoline
4,4-Dimethyl-2-(2-dodecyl)-2-oxazoline
2-(Methyl-2-decyl)-2-oxazoline
4,4-Dimethyl-2-(2-methyl-2-decyl)-2-oxazoline
4-Methyl-4-[1-(2-oxadodecyl)]-2-trifluoromethyl-2-oxazoline
4,4-Dimethyl-2-[1-(3-oxaundecyl)]-2-oxazoline
1-(2-Hydroxyethyl)-2-undecyl-2-imidazoline
1-(2-Ethoxyethyl)-2-undecyl-2-imidazoline
1-(2-Carbethoxyethyl)-2-undecyl-2-imidazoline
1-(2-Hydroxyethyl)-2-undecyl-2-imidazoline acetate
4-Decyl-2-trifluoromethyl-2-imidazoline
1-Dodecyl-2-trifluoromethyl-2-imidazoline
4-Dodecyl-2-ethoxy-2-imidazoline
4-Dodecyl-2-ethoxy-2-oxazoline The next preceeding list of compounds, along with 4-Decyl-2-trifluoromethyl-2-oxazoline have been found to be significantly superior penetration enhancing agents, both as compared with the prior art and as compared with the other examples given herein.

While particular embodiments of the invention have been described it will be understood of course that the invention is not limited thereto since many obvious modifications can be made and it is intended to include within this invention any such modifications as will fall within the scope of appended claims.

Industrial Application

This invention is useful in the pharmaceutical and agricultural industries and in the preparation of compositions for cosmetic, diagnostic and therapeutic use.

What is claimed is:

1. A pharmaceutical composition for enhancing absorption of a topically administered formulation through dermal or mucosal membrane, for local or systemic application, comprising a therapeutically effective amount of a pharmaceutically active cardiovascular agent and a non-toxic, effective amount of a membrane penetration enhancing agent of formula I:

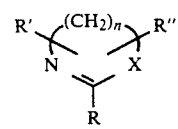

wherein R is a saturated or unsaturated, straight or branched, cyclic or acyclic hydrocarbon group with from 1 to 19 carbon atoms, alkoxyalkyl, haloalkyl, specifically trifluoromethyl, alkoxy, amino, alkylamino and acylamino; R' and R" are hydrogen, alkyl, trifluoromethyl, alkoxyalkyl, aminoalky, alkyl- and acylaminoalkyl, carboxy, carbalkoxy, hydroxyalkyl or lower alkyl ester thereof; X is O or $NR_1$ wherein $R_1$ is hydrogen, alkyl, alkenyl, alkoxyalkyl, carbalkoxyalkyl, aminoalkyl, alkyl- and acylaminoalkyl, hydroxyalkyl or hydroxyalkyloxyalkyl and lower alkyl ester thereof; and n is 2 or 3.

2. The composition of claim 1 wherein the membrane penetration enhancing agent is represented by formula I wherein R is alkyl, alkoxy, haloalkyl or alkoxyalkyl, R' and R'' are H, alkyl or alkoxyalkyl; X is O or $NR_1$, wherein $R_1$ is hydrogen, carbalkoxyalkyl, alkoxyalkyl, hydroxyalkyl, hydroxyalkyloxyalkyl and lower alkyl esters thereof and n is 2 or 3.

3. The composition of claim 2 wherein said pharmaceutically active agent is a cardiovascular agent selected from the group consisting of isosorbide dinitrate, clonidine, propranolol, nifedipine, nicardipine, diltiazem, and lisinopril.

4. The composition of claim 1 further comprising pharmaceutically acceptable excipients.

5. A method of enhancing the rate of dermal or mucosal membrane absorption of a topically administered composition for local or systemic application, comprising applying to the skin of a human or an another animal a therapeutically effective dosage amount of a pharmaceutically active cardiovascular agent and a non-toxic, effective amount of a membrane penetration enhancing agent of formula I:

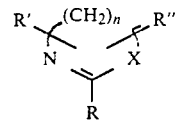

wherein R is a saturated or unsaturated, straight or branched, cyclic or acyclic hydrocarbon group with from 1 to 19 carbon atoms, alkoxyalkyl, haloalkyl, specifically trifluoromethyl, alkoxy, amino, alkylamino and acylamino; R' and R'' are hydrogen, alkyl, trifluoromethyl, alkoxyalkyl, aminoalkyl, alkyl- and acylaminoalkyl, carboxy, carbalkoxy, hydroxyalkyl or lower alkyl ester thereof; X is O or $NR_1$ wherein $R_1$ is hydrogen, alkyl, alkenyl, alkoxyalkyl, carbalkoxyalkyl, aminoalkyl, alkyl- and acylaminoalkyl, hydroxyalkyl or hydroxyalkyloxyalkyl and lower alkyl ester thereof; and n is 2 or 3.

6. The method of claim 5 wherein the membrane penetration enhancing agent is represented by formula I wherein R is alkyl, alkoxy, haloalkyl or alkoxyalkyl, R' and R'' are, H, alkyl or alkoxyalkyl; X is O or $NR_1$ wherein $R_1$ is hydrogen, carbalkoxyalkyl, alkoxyalkyl, hydroxyalkyl, hydroxyalkyloxyalkyl and lower alkyl esters thereof and n is 2 or 3.

7. The method of claim 6 wherein said pharmaceutically active agent is a cardiovascular agent selected from the group consisting of isosorbide dinitrate, clonidine, propranolol, nifedipine, nicardipine, diltiazem, and lisinopril.

* * * * *